United States Patent
Eisenacht et al.

[11] Patent Number: 6,166,259
[45] Date of Patent: Dec. 26, 2000

[54] PROCESS FOR PREPARING A 1,1,1-TRIFLUORO-2-AMINOALKANE

[75] Inventors: Rudi Eisenacht, Mainz; Hans-Peter Niedermann, Bubenheim; Dieter Landau, Flonheim, all of Germany

[73] Assignee: American Cyanamid Company, Madison, N.J.

[21] Appl. No.: 09/537,196

[22] Filed: Mar. 28, 2000

Related U.S. Application Data

[60] Provisional application No. 60/129,460, Apr. 15, 1999.

[51] Int. Cl.$^7$ .................................................. C07C 209/52
[52] U.S. Cl. ........................... 564/486; 560/172; 562/574
[58] Field of Search ........................... 564/486; 560/172; 562/574

[56] References Cited

U.S. PATENT DOCUMENTS

| | | | |
|---|---|---|---|
| 4,840,969 | 6/1989 | Tarnow et al. ........................... | 514/617 |
| 5,082,862 | 1/1992 | Harnow et al. ........................... | 514/617 |
| 5,593,996 | 1/1997 | Pees et al. ............................... | 514/258 |

FOREIGN PATENT DOCUMENTS

| | | | |
|---|---|---|---|
| 3611193 A1 | 10/1987 | Germany ...................... | C07C 103/76 |
| WO 98/46608 | 10/1998 | WIPO .......................... | C07D 487/04 |

OTHER PUBLICATIONS

Tetrahedron Letters, vol. 35, No. 19, pp. 3119–3122, Soloshonok et al., A practical route to fluoroalkyl– and fluoroarylamines by base–catalyzed [1,3]–proton shift reaction, 1994.

T. Ono et al., "Biomimetic Reductive Amination of Fluoro Aldehydes and Ketones via [1,3]–Proton Shift Reaction. Scope and Limitations", J. Org. Chem. 1996, 61, 6563–6569.

*Primary Examiner*—Samuel Barts
*Assistant Examiner*—Brian J. Davis
*Attorney, Agent, or Firm*—Charles F. Costello

[57] ABSTRACT

The invention relates to a process for the preparation of a 1,1,1-trifluoro-2-aminoalkane of formula I

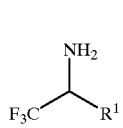

(I)

wherein $R^1$ represents an optionally substituted alkyl group; which comprises heating a mixture consisting essentially of a compound of formula II

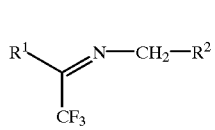

(II)

wherein $R^1$ has the meaning given, and $R^2$ represents an optionally substituted aryl group, a primary amine, and optionally a base and/or an inert diluent, whereby the compound of formula I is removed by distillation during the heating procedure.

13 Claims, No Drawings

PROCESS FOR PREPARING A 1,1,1-TRIFLUORO-2-AMINOALKANE

This application claims priority from copending provisional application(s) serial number 60/129,460 filed on Apr. 15, 1999.

BACKGROUND OF THE INVENTION

The invention relates to a novel process for the preparation of 1,1,1-trifluoro-2-aminoalkanes which comprises reacting the corresponding N-alkylidene benzylamines with a primary amine whereby the product compound is removed by distillation.

1,1,1-trifluoro-2-aminoalkanes are useful as intermediates for the preparation of a variety of compounds which are useful as agrochemicals, pharmaceuticals or dyes. In particular, they are key intermediates in the preparation of insecticidal benzamides as disclosed for example by DE 36 11 193 and of fungicidal 7-(1,1,1-trifluoroalk-2-ylamino)-6-(halophenyl)-triazolopyrimidines which are described for example in WO 98/46608.

T. Ono, et al., J. Org. Chem. 61,1996, 6563–6569 disclose a method for the preparation of 1,1,1-trifluoro-2-aminopropane by rearrangement of N-(1,1,1-triflluoroisopropylidene)benzylamine to N-benzylidene-1,1,1-trifluoroisopropylamine. The resulting benzylidene compound is hydrolyzed to the amine hydrochloride with hydrochloric acid using ether as diluent. The amine hydrochloride is separated from the benzaldehyde and the free amine is prepared by action of triethylamine on the amine hydrochloride.

Thus the process known from the art requires several steps to yield the desired 1,1,1-trifluoro-2-aminoalkanes. The novel process has been found to be advantageous in producing 1,1,1-trifluoro-2-aminoalkanes in only up to two steps.

SUMMARY OF THE INVENTION

The 1,1,1-trifluoro-2-aminoalkanes of formula I

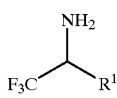

(I)

wherein $R^1$ represents an optionally substituted alkyl group;

can be obtained in high yields by heating a mixture consisting essentially of a compound of formula II

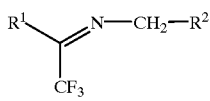

(II)

wherein $R^1$ has the meaning given, and $R^2$ represents an optionally substituted aryl group;

a primary amine, and optionally a base and/or an inert diluent, whereby the compound of formula I is removed by distillation during the heating procedure.

It is an object of the present invention to provide an efficient new process for the preparation of 1,1,1-trifluoro-2-aminoalkanes of formula I.

Other objects and advantages of the present invention will be apparent to those skilled in the art from the following description and the appended claims.

DETAILED DESCRIPTION OF THE PREFERRED EMBODIMENTS

The invention relates to a novel process for the preparation of the compounds of formula I by heating a mixture consisting essentially of a compound of formula II, a primary amine and optionally a base and/or an inert diluent. The advantage of the novel process is, that the compound of formula I is obtained directly in high yields and high purity by distillation during the heating procedure.

In general terms, unless otherwise stated herein, the term alkyl as used herein with respect to a radical or moiety refers to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A particularly preferred alkyl moiety is the methyl group.

In general terms, unless otherwise stated herein, the term aryl as used herein with respect to a radical or moiety refers to an aryl group having 6, 10 or 14 carbon atoms, preferably 6 or 10 carbon atoms. A particularly preferred aryl moiety is the phenyl group being optionally substituted by one or more halogen atoms, nitro, cyano, alkyl, preferably $C_{1-8}$ alkyl, alkoxy, preferably $C_{1-6}$ alkoxy.

Suitable primary amines are primary amines having 2 to 20 carbon atoms, preferably 6 to 14 carbon atoms. Preferred are primary amines having a boiling point higher than the boiling point of the compound of formula I in particular aralkylamines being optionally substituted by one or more halogen atoms, alkyl, preferably $C_{1-6}$ alkyl, alkoxy, preferably $C_{1-6}$ alkoxy, most preferably benzylamine.

Preferably the reaction is carried out with a compound of formula II to primary amine molar ratio from 1:1 to 1:1.5, in particular from 1:1.1 to 1:1.3, most preferred at a ratio of about 1:1.2.

Suitable inert diluents are cyclic ethers, aliphatic ethers, aliphatic hydrocarbons or aromatic hydrocarbons. Most preferred are aromatic hydrocarbons having 6 to 14 carbon atoms, in particular benzene, toluene, xylene or mesitylene.

Suitable bases are tertiary amines, in particular bicyclic tertiary amines, such as 1,8-diazabicyclo [5.4.0]undecene-7 (DBU) or 1,5diazabicyclo [3.4.0]nonene-5 (DBN).

Preferably the reaction is carried out in the presence of catalytic amounts of a base, in particular at a compound of formula II to base molar ratio from 1:0.001 to 1:0.1, most preferred from 1:0.005 to 1: 0.05.

A preferred embodiment of the present invention is a process wherein:

the reaction is carried out at temperatures between 80 and 140° C.; preferably between 90° C. and 130° C., in particular between 95° C. and 120 C.; most preferred at about 115° C.;

the reaction is carried out at atmospheric pressure;

the reaction mixture consists of a compound of formula II, a primary amine and a catalytic amount of a base, preferably DBU.

$R^1$ represents a $C_{1-4}$ alkyl group being optionally substituted by one or more halogen atoms or an alkoxycarbonyl or hydroxycarbonyl group, in particular wherein $R^1$ represents a methyl group;

The compound of formula II is most preferably N-(1,1,1-trifluoroisopropylidene)benzylamine. The compound of formula II can be prepared by a condensation reaction between commercially available 1,1,1-trifluoro-2-oxoalkane and benzylamine or a salt thereof as disclosed for example T. Ono, et al., loc. cit.

In a preferred embodiment of the invention the preparation of the compound of formula I is carried out in a one-pot synthesis comprising the steps of a) condensation of a 1,1,1-trifluoro-2-oxo-alkane of formula III,

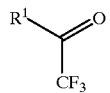
(III)

and an optionally substituted benzylamine, of formula IV,

(IV)

preferably by azeotropic removal of the water formed during the reaction with the aid of an inert aromatic diluent in the presence of an acid, preferably p-toluenesulfonic acid, and b) treating the resulting N-(1,1,1-trifluoroalkyliden-2-yl) benzylamine with a primary amine in the presence of a base and/or an inert aromatic diluent at elevated temperatures, whereby the desired compound of formula I distills off.

After the condensation step (a), preferably using mixture of mesitylene and toluene as an inert diluent in the presence of p-toluenesulfonic acid the reaction water together optionally with the low boiling diluent, preferably toluene, is separated via a water separator. An excess of the primary amine and catalytic amounts of the base, preferably benzylamine and DBU are added at a temperature from 70° C. to 120° C., in particular at about 90° C. and the liberated compound of formula I is rectificated over a column and collected in an ice cooled trap The crude product obtained can be purified according to standard methods for example by distillation, recrystallization or chromatographic methods.

However, the crude product obtained according to the process of this invention is as a rule pure enough to be used as intermediate without further purification.

In a particularly preferred embodiment of the process according to this invention a mixture of the compound of formula II, in particular N-(1,1,1-trifluoroisopropylidene) benzylamine, a primary amine, preferably benzylamine and a catalytic amount of a base, preferably DBU is heated at a temperature of about 115° C. The amine of formula 1, in particular 2-amino-1,1,1-trifluoropropane, is obtained by distillation during the reaction. The reaction temperature of about 115° C. is kept until no further amine distills off.

In order to facilitate a further understanding of the invention, the following illustrative examples are presented. The invention is not limited to the specific embodiments described or illustrated, but encompasses the full scope of the appended claims.

Example 1
Preparation of N-(1,1,1-trifluoroisopropylidene) benzylamine 3360 g of 1,1,1-trifluoroacetone were added to a solution of 1,5 g of p-toluenesulfonic acid in 10 l toluene after cooling down to 0° C. Subsequently, 3225 g of benzylamine were dosed within 3 hours at a temperature range of 0 to 10° C. The reaction mixture was heated with reflux for 15 hours.

The reaction water was distilled off and subsequently the mixture cooled to room temperature. The solvent was removed in vacuo to yield 5420 g of a crude mixture containing 71,7% of N-(1,1,1-trifluoroisopropylidene) benzylamine. The mixture was used for the preparation of 2-amino-1,1,1-trifluoropropane without further purification.

Example 2
Preparation of 2-amino-1,1,1-trifluoropropane 4643 g of N-(1,1,1-trifluoroisopropylidene) benzylamine obtained in Example 1 were placed in a three necked flask with stirrer, dropping funnel and descending condenser with an ice-cooled flask. 2755 g of benzylamine were added and the mixture was heated up to 90° C. 20 ml of DBU were added and the 2-amino-1,1,1-trifluoropropane started to distill off. The reaction mixture was heated up to 115° C. and subsequently 25 ml of DBU were added. The reaction temperature was kept at 115° C. until no further 2-amino-1,1,1-trifluoropropane distilled off. 1857 g of the pure product were collected having a boiling point of 46–47° C.

Example 3
Preparation of 2-amino-1,1,1-trifluoropropane

In a three necked flask with reflux condenser and dropping funnel a mixture of 300 ml toluene, 200 ml mesitylene, 112 g 1,1,1-trifluoroacetone and 0,5 g of p-toluene sulfonic acid was cooled to 0° C. with magnetical stirring. To this mixture 112,5 g benzylamine was added dropwise keeping the temperature below 10° C. The reaction mixture was heated to reflux over night. After cooling to room temperature the reflux condenser was substituted by a Dean-Stark trap and the mixture heated to reflux to separate the reaction water.

After separation of the reaction water the mixture was cooled to room temperature and the Dean-Stark trap was substituted by a rectification unit. A mixture of 153 g benzylamine and 2 ml DBU was slowly added and the mixture was heated to 95° C. 2-Amino-1,1,1-trifluoropropane distilled of and was collected in an ice cooled trap. Another 28 ml of DBU was added portionwise until no 2-amino-1,1,1-trifluoropropane distilled off. Yield: 77 g.

What is claimed is:

1. A process for the preparation of a 1,1,1-trifluoro-2-aminoalkane of formula I

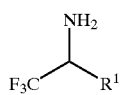
(I)

wherein $R^1$ represents an optionally substituted alkyl group;

which comprises heating a mixture consisting essentially of a compound of formula II

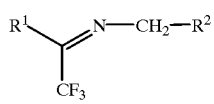
(II)

wherein

R[1] has the meaning given, and

R[2] represents an optionally substituted aryl group;

a primary amine, and optionally a base and/or an inert diluent, whereby the compound of formula I is removed by distillation during the heating procedure.

2. A process according to claim 1, wherein the reaction is carried out at a temperature from 80° C. to 140° C.

3. A process according to claim 1, wherein the reaction is carried out at atmospheric pressure.

4. A process according to claim 1, wherein the diluent is an optionally substituted aromatic hydrocarbon.

5. A process according to claim 4, wherein the compound of formula II to primary amine molar ratio is from 1:1 to 1:1.5.

6. A process according to claim 1, wherein the primary amine has a boiling point higher than the boiling point of the compound of formula I.

7. A process according to claim 1, wherein the primary amine is an optionally substituted benzylamine.

8. A process according to claim 1, wherein a tertiary amine is used as a base.

9. A process according to claim 8, wherein the tertiary amine is 1,8-diazabicyclo[5.4.0]undecene-7 (DBU).

10. A process according to claim 1, which comprises the steps of:

a) condensation of a 1,1,1-trifluoro-2-oxo-alkane of formula III,

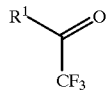

(III)

wherein R[1] has the meaning given, and an optionally substituted benzylamine of formula IV,

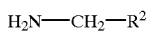

(IV)

wherein R[2] has the meaning given, by azeotropic removal of the water formed during the reaction with the aid of an inert aromatic diluent; and b) treating the resulting N-(1,1,1-trifluoroalkyliden-2-yl) benzylamine with a primary amine in the presence of a base and/or an inert aromatic diluent at elevated temperatures, whereby the desired compound of formula I distills off.

11. A process according to claim 1, wherein R[1] represents a $C_{1-4}$ alkyl group being optionally substituted by one or more halogen atoms or an alkoxycarbonyl group.

12. A process according to claim 11, wherein R[1] represents a methyl group.

13. A process according to claim 4 wherein the aromatic hydrocarbon is toluene, xylene or mesitylene.

* * * * *